US007960465B2

(12) United States Patent
Rathore et al.

(10) Patent No.: US 7,960,465 B2
(45) Date of Patent: Jun. 14, 2011

(54) ANTIMICROBIAL LENSES, PROCESSES TO PREPARE THEM AND METHODS OF THEIR USE

(75) Inventors: Osman Rathore, Jacksonville, FL (US); Azaam Alli, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 666 days.

(21) Appl. No.: 11/757,484

(22) Filed: Jun. 4, 2007

(65) Prior Publication Data

US 2008/0273168 A1    Nov. 6, 2008

Related U.S. Application Data

(60) Provisional application No. 60/806,346, filed on Jun. 30, 2006.

(51) Int. Cl.
*C08K 3/08* (2006.01)
*C08K 3/34* (2006.01)

(52) U.S. Cl. .................... 524/430; 351/160 H
(58) Field of Classification Search .................. 524/430; 351/160 H
See application file for complete search history.

(56) References Cited

U.S. PATENT DOCUMENTS

| 3,408,429 | A | 10/1968 | Wichterle |
|---|---|---|---|
| 3,660,545 | A | 5/1972 | Wichterle |
| 3,808,178 | A | 4/1974 | Gaylord |
| 4,113,224 | A | 9/1978 | Clark |
| 4,120,570 | A | 10/1978 | Gaylord |
| 4,136,250 | A | 1/1979 | Mueller |
| 4,153,641 | A | 5/1979 | Deichert |
| 4,197,266 | A | 4/1980 | Clark |
| 4,495,313 | A | 1/1985 | Larsen |
| 4,680,336 | A | 7/1987 | Larsen |
| 4,740,533 | A | 4/1988 | Su |
| 4,889,664 | A | 12/1989 | Kindt Larsen |
| 4,910,277 | A | 3/1990 | Bambury |
| 4,973,493 | A | 11/1990 | Guire |
| 5,034,461 | A | 7/1991 | Lai |
| 5,039,459 | A | 8/1991 | Kindt Larsen |
| 5,070,215 | A | 12/1991 | Bambury |
| 5,135,297 | A | 8/1992 | Valint, Jr. |
| 5,275,838 | A | 1/1994 | Merrill |
| 5,321,108 | A | 6/1994 | Kunzler |
| 5,387,662 | A | 2/1995 | Kunzler |
| 5,539,016 | A | 7/1996 | Kunzler |
| 5,760,100 | A | 6/1998 | Nicolson |
| 5,779,943 | A | 7/1998 | Enns |
| 5,944,853 | A | 8/1999 | Molock |
| 6,087,415 | A | 7/2000 | Vanderlaan |
| 6,193,369 | B1 | 2/2001 | Valint, Jr. |
| 6,200,626 | B1 | 3/2001 | Grobe, III |
| 6,213,604 | B1 | 4/2001 | Valint, Jr. |
| 6,475,970 | B1 | 11/2002 | Del Duca et al. |
| 6,846,892 | B2 | 1/2005 | Kindt Larsen |
| 2002/0016383 | A1 | 2/2002 | Iwata |
| 2003/0043341 | A1* | 3/2003 | Turner et al. .............. 351/160 R |
| 2003/0044447 | A1 | 3/2003 | Zanini et al. |
| 2003/0052424 | A1 | 3/2003 | Turner |
| 2003/0162862 | A1 | 8/2003 | McCabe |
| 2004/0150788 | A1* | 8/2004 | Andersson et al. ....... 351/160 R |
| 2005/0006640 | A1 | 1/2005 | Jackson |
| 2006/0072069 | A1 | 4/2006 | Laredo |

FOREIGN PATENT DOCUMENTS

| DE | 10024363 A1 | 11/2001 |
|---|---|---|
| EP | 0080539 | 6/1983 |
| EP | 1050314 | 11/2000 |
| WO | WO 96/31792 | 10/1996 |
| WO | WO 02/062402 | 8/2002 |
| WO | WO 03/003073 | 1/2003 |
| WO | WO 03/011351 A2 | 2/2003 |
| WO | WO 03/011551 | 2/2003 |
| WO | WO 2006/012000 A1 | 2/2006 |
| WO | WO 2006/039276 | 4/2006 |

OTHER PUBLICATIONS

Contact Lens Practice, Chapman & Hall, 1994, edited by M. Ruben and M. Guillon, pp. 589-599.
Volume III, Photoinitiators for Free Radical Cationic & Anionic Photopolymerization, $2^{nd}$ Edition by J.V. Crivello & K. Dietliker; edited by G. Bradley; John Wiley and Sons; New York; 1998.
CRC Handbook of Chemistry and Physics, $74^{th}$ Edition, CRC Press, Boca Raton Florida, 1993.
Skoog, D.A. et al. Fundamentals of Analytical Chemistry, Fifth Edition, Saunders College Publishing, New York, 1988.

* cited by examiner

*Primary Examiner* — David Wu
*Assistant Examiner* — Chun-Cheng Wang
(74) *Attorney, Agent, or Firm* — Karen Harding

(57) ABSTRACT

The present invention relates to contact lenses comprising at least one ionizable antimicrobial metal compound and a polymer formed from a reaction mixture comprising at least one hydrophobic component and hydrophilic components in a concentration to provide a hydrophilicity index of at least 42.

27 Claims, No Drawings

ANTIMICROBIAL LENSES, PROCESSES TO PREPARE THEM AND METHODS OF THEIR USE

RELATED APPLICATIONS

This application claims priority to a provisional application U.S. Ser. No. 60/806,346, filed on Jun. 30, 2006, which is incorporated herein in its entirety.

FIELD OF THE INVENTION

This invention relates to antimicrobial lenses as well as methods of their production, and use.

BACKGROUND OF THE INVENTION

Contact lenses have been used commercially to improve vision since the 1950s. The first contact lenses were made of hard materials. They were used by a patient during waking hours and removed for cleaning. Current developments in the field gave rise to soft contact lenses, which may be worn continuously, for several days or more without removal for cleaning. Although many patients favor these lenses due to their increased comfort, these lenses can cause some adverse reactions to the user. The extended use of the lenses can encourage the buildup of bacteria or other microbes, particularly, *Pseudomonas aeruginosa*, on the surfaces of soft contact lenses. The build-up of bacteria and other microbes can cause adverse side effects such as contact lens acute red eye and the like. Although the problem of bacteria and other microbes is most often associated with the extended use of soft contact lenses, the build-up of bacteria and other microbes occurs for users of hard contact lens wearers as well.

Medical devices made from a water absorbable polymer material with a medical compound having low solubility in aqueous solutions such as an antiseptic or radiopaque compound have been disclosed Medical devices, including contact lenses containing reduced or metallic silver have also been disclosed.

However, the need remains for contact lenses that inhibit the growth of bacteria or other microbes and/or the adhesion of bacteria or other microbes on the surface of contact lenses. Further there is a need to produce contact lenses which do not promote the adhesion and/or growth of bacteria or other microbes on the surface of the contact lenses. Also there is a need to produce contact lenses that inhibit adverse responses related to the growth of bacteria or other microbes.

SUMMARY OF THE INVENTION

The present invention relates to contact lenses comprising at least one metal salt and a polymer formed from a reaction mixture comprising at least one hydrophobic component and hydrophilic components in a concentration to provide a hydrophilicity index of at least about 42.

The present invention further relates to contact lenses comprising at least one ionizable antimicrobial metal compound and a polymer formed from a reaction mixture comprising at least one hydrophobic component and hydrophilic components in a concentration to provide a hydrophilicity index of at least 42.

DETAILED DESCRIPTION OF THE INVENTION

The present invention relates to antimicrobial lenses comprising, consisting essentially of, or consisting of a metal salt that display acceptable on eye movement, as defined below. As used herein, the term, "antimicrobial lens" means a lens that exhibits one or more of the following properties, the inhibition of the adhesion of bacteria or other microbes to the lenses, the inhibition of the growth or proliferation of bacteria or other microbes on lenses, and the killing of bacteria or other microbes on the surface of lenses or in an area surrounding the lenses. For purposes of this invention, adhesion of bacteria or other microbes to lenses, the growth of bacteria or other microbes on lenses and the presence of bacteria or other microbes on the surface of lenses are collectively referred to as "microbial colonization." Preferably, the lenses of the invention exhibit a reduction of viable bacteria or other microbe of at least about 0.5 log, and in some embodiments at least about 1.0 log ($\geq$90% inhibition). Such bacteria or other microbes include but are not limited to those organisms found in the eye, particularly *Pseudomonas aeruginosa*, *Acanthamoeba* species, *Staphyloccus. aureus*, *E. coli*, *Staphylococcus epidermidis*, *Serratia marcesens* and *Fusarium solani*.

As used herein the term "ionizable antimicrobial metal compound" means any compound comprising an antimicrobial metal cation capable of disassociating from the compound and eluting from the ophthalmic device and a binding component capable of releasably binding said antimicrobial metal cation. The antimicrobial metal cation may be selected from the positively charged metals, M, defined below. The binding component may be selected from ligands, zeolites and negatively charges ions X, defined below. Suitable examples of zeolites are aluminosilicates, such as those disclosed in EP 1,050,314 and US2003-0043341. Suitable examples of ligands include reactive ligands which can be polymerized into the lens polymer such as those is disclosed in US2003-0044447 and ligands which when bound to the antimicrobial metal cation form a sparingly soluble complex.

As use herein, the term "metal salt" means any molecule having the general formula $[M]_a [X]_b$ wherein X contains any negatively charged ion, a is $\geq$1, b is $\geq$1 and M is any positively charged metal selected from, but not limited to, the following $Al^{+3}$, $Co^{+2}$, $Co^{+3}$, $Ca^{+2}$, $Mg^{+2}$, $Ni^{+2}$, $Ti^{+2}$, $Ti^{+3}$, $Ti^{+4}$, $V^{+2}$ $V^{+3}$, $V^{+5}$, $Sr^{+2}$, $Fe^{+2}$, $Fe^{+3}$, $Au^{+2}$, $Au^{+3}$, $Au^{+1}$, $Pd^{+2}$, $Pd^{+4}$, $Pt^{+2}$, $Pt^{+4}$, $Cu^{+1}$, $Cu^{+2}$, $Mn^{+2}$, $Mn^{+3}$, $Mn^{+4}$, $Zn^{+2}$, combinations thereof and the like. Examples of X include but are not limited to $CO_3^{-2}$, $NO_3^{-1}$, $PO_4^{-3}$, $Cl^{-1}$, $I^{-1}$, $Br^{+2}$, $O^{-2}$ combinations thereof and the like. Further, in some embodiments X includes negatively charged ions containing $CO_3^{-2}$, $SO_4^{-2}$, $CH_3CO_2^{-1}$, $PO_4^{-3}$, $Cl^{-1}$, $Br^{-1}$, $S^{-2}$ and $O^{-2}$, combinations thereof and the like, such as $C_{1-5}alkylCO_2^{-1}$. In yet other embodiments X includes $CO_3^{-2}$, $SO_4^{-2}$, $Cl^{-1}$, $I^{-1}$, and $Br^{-1}$, and mixtures thereof. As used herein the term metal salts does not include zeolites, disclosed in WO03/011351, This patent application, and all other applications, patents and publications cited herein, are hereby incorporated by reference in its entirety. In one embodiment a is 1, 2, or 3. In one embodiment b is b 2, or 3. In one embodiment the metals ions are $Mg^{+2}$, $Zn^{+2}$, $Cu^{+1}$, $Cu^{+2}$, $Au^{+2}$, $Au^{+3}$, $Au^{+1}$, $Pd^{+2}$, $Pd^{+4}$, $Pt^{+2}$, $Pt^{+4}$, $Ag^{+2}$, and $Ag^{+1}$ and mixtures thereof. In another embodiment the metal ion comprises $Zn^{+2}$, $Cu^{+1}$, $Cu^{+2}$, $Ag^{+2}$, $Ag^{+1}$ and mixtures thereof. In another embodiment the metal ion comprises $Ag^{+1}$. In another embodiment the metal ion is $Ag^{+1}$. Examples of suitable metal salts include but are not limited to manganese sulfide, zinc oxide, zinc sulfide, copper sulfide, and copper phosphate. Examples of silver salts include but are not limited to silver sulfate, silver iodate, silver carbonate, silver phosphate, silver sulfide, silver chloride, silver bromide, silver iodide, and silver oxide. In one embodiment the silver salts are silver iodide, silver chloride, and silver bromide. In another embodiment the silver salt comprises silver iodide.

The lenses of the invention are ophthalmic lenses (a detailed description of these lenses follows) and the clarity of the lenses is of concern to users. In order to produce lenses having a clarity suitable for ophthalmic purposes, it is desired that the diameter of the metal salt particles is less than about ten microns (10 μm), in some embodiments less than about 5 μM, and in some embodiments equal to or less than about 200 nm.

The amount of metal in the lenses is measured based upon the total weight of the lenses. When the metal is silver, the preferred amount of silver is about 0.00001 weight percent (0.1 ppm) to about 10.0 weight percent, preferably about 0.0001 weight percent (1 ppm) to about 1.0 weight percent, most preferably about 0.001 weight percent (10 ppm) to about 0.1 weight percent, based on the dry weight of the lens. With respect to adding metal salts, the molecular weight of the metal salts determines the conversion of weight percent of metal ion to metal salt. The preferred amount of silver salt is about 0.00003 weight percent (0.3 ppm) to about 30.0 weight percent, preferably about 0.0003 weight percent (3 ppm) to about 3.0 weight percent, most preferably about 0.003 weight percent (30 ppm) to about 0.3 weight percent, based on the dr weight of the lens.

As used herein, the +term "lens" refers to an ophthalmic device that resides in or on the eye. These devices can provide optical correction, wound care, drug delivery, diagnostic functionality, cosmetic enhancement or effect or a combination of these properties. The term lens includes but is not limited to soft contact lenses, hard contact lenses, intraocular lenses, overlay lenses, ocular inserts, and optical inserts. The lenses of the invention are optically clear, with optical clarity comparable to lenses such as lenses made from etafilcon A.

As used herein "acceptable movement on eye" means observable movement on at least the Josephson's push up test, after at least one hour of wear, in some embodiments after at least about 4 hours of wear, and in other embodiments after at least about 8 hours of wear. In the Josephson's push up test, movement is measured after at least a minimum of 30 minutes lens settling, by judging the resistance to lens movement upon light digital pressure on the lower lid while the patient looks straight ahead. The Josephson push up test is described in detail in Contact Lens Practice, Chapman & Hall, 1994, edited by M. Ruben and M. Guillon, pgs. 589-99. Any observable movement is indicative of acceptable movement on eye.

It has been found that when a certain population of contact lens wearers wear silicone hydrogel contact lenses comprising at least one antimicrobial metal salt, the lenses do not display any on eye movement using the Josephson's push up test, particularly after several hours of wear. Applicants have surprisingly found that when the formulation has a hydrophilicity index of greater than about 42, and in some embodiments greater than about 44, and in other embodiments greater than about 45, the lenses display acceptable on-eye movement when evaluated using the Josephson's push up test in substantially all patients. It was also found that substantially all patients displayed observable on eye movement in primary gaze and up gaze lens movement assessments. In these assessments, the patients are asked to blink and look either forward or up. The vertical lens movement after blinking is subjectively graded using the following scale. $-2$=unacceptable, no observable movement, $-1$=minimal, but acceptable movement, 0 optimal movement, $+1$ moderate but acceptable movement, $+2$=excessive movement, unacceptable. In one embodiment, lenses of the present invention were also found to have ratings in at least one of the primary and up gaze assessments of at least $-1$ and in some embodiments between $-1$ and 0.

The hydrophilicity index is the sum of the relative hydrophilic contribution of each of the hydrophilic components in the monomer mix and may be calculated as follows. The hydrophilic contribution is the increase in water content provided to the final polymer by each component that is at least as hydrophilic as 2-hydroxyethyl methacrylate (HEMA). The hydrophilic contribution may be calculated by making a series of formulations with 0, 0.5, 1 and 2 wt % hydrophilic component whose hydrophilic contribution is being determined. In each formulation the amount of HEMA is decreased by the amount of hydrophilic component added. The base formulation used for the measurements is 28 wt % SiMAA,
31 wt % mPDMS 1000 (commercially available from Gelest)
24 wt % DMA
8 wt % 2-hydroxyethyl methacrylate,
1.5 wt % TEGDMA
7 wt % PVP (360,000) and
0.5 wt % CGI 819 (commercially available from Ciba Specialty Chemicals).

For example, if the hydrophilic contribution of methacrylic acid (MAA) were being determined, the four formulations made would be:

|  | 1 | 2 | 3 | 4 |
| --- | --- | --- | --- | --- |
| SiMMA | 28 | 28 | 28 | 28 |
| MPDMS | 31 | 31 | 31 | 31 |
| DMA | 24 | 24 | 24 | 24 |
| HEMA | 8 | 7.5 | 7 | 6 |
| MAA | 0 | 0.5 | 1 | 2 |
| TEGDMA | 1.5 | 1.5 | 1.5 | 1.5 |
| PVP | 7 | 7 | 7 | 7 |
| CGI 819 | 0.5 | 0.5 | 0.5 | 0.5 |

Each formulation is mixed in 3,7-dimethyl-3-octanol in a 75:25 reactive component:diluent ratio and cured in contact lens molds (Zeonor front curve, polypropylene back curve) under visible light (Philips TL-03 bulbs) in a nitrogen atmosphere (<0.5% $O_2$) @45°±5° C. for about 30 minutes. The resulting lenses are released from the molds and solvent exchanged as described in the Examples, under procedure 2. The water content for each formulation is measured as described herein. The water content is graphed as a function of the hydrophilic component being measured (in this case methacrylic acid) and the slope of the resulting line is the hydrophilic contribution. So, for methacrylic acid, the hydrophilic contribution is 6. The hydrophilicity contributions, measured by the process above, for DMA and PVP are 1 and 2, respectively.

In these examples, HEMA was used as the variable hydrophilic component, and thus its hydrophilicity index cannot be measured using the process above. However, the water content of a HEMA homopolymer made with 1.5 wt % crosslinker is about 40%. The hydrophilicity contribution assigned to HEMA is 0.4.

The hydrophilicity index is the sum of the products of the concentration of the hydrophilic component and its hydrophilic contribution. For the base formulation described above, containing 24 wt % DMA, 8 w % HEMA and 7% PVP, the hydrophilicity index is $(1\times24)+(0.4\times8)+(2\times7)=41.2$.

Polymeric and macromer components may also contribute to the hydrophilicity of the resulting polymer. The hydrophilicity contribution of hydrophilic polymers and macromers which are non-reactive such as PVP) or have only one reactive group and contain any hydrophilic functionality is measured and calculated as described above. For multifunctional hydrophilic components the hydrophilic contribution may be ascertained by using a monofunctional equivalent and following the procedure described above.

The lenses of the present invention may include almost any other components, so long as hydrophilic components are present in quantities sufficient to provide the hydrophilicity indices specified herein.

The reactive mixtures of the present invention comprise at least one hydrophilic component, in concentrations sufficient to provide the hydrophilicity indices disclosed herein. Hydrophilic components are those which when mixed, at 25° C. in a 1:1 ratio by volume with neutral, buffered water (pH about 7.0) forms a homogenous solution, Any of the hydrophilic monomers known to be useful to make hydrogels may be used.

One class of suitable hydrophilic monomers include acrylic- or vinyl-containing monomers. Such hydrophilic monomers may themselves be is used as crosslinking agents, however, where hydrophilic monomers having more than one polymerizable functional group are used, their concentration should be limited as discussed below to provide a contact lens having the desired modulus. The term "vinyl-type" or "vinyl-containing" monomers refer to monomers containing the vinyl grouping (—CH=CH$_2$) and are generally highly reactive. Such hydrophilic vinyl-containing monomers are known to polymerize relatively easily. Hydrophilic vinyl-containing monomers which may be incorporated into the silicone hydrogels of the present invention include monomers such as N-vinyl amides, N-vinyl lactams (e.g. N-vinylpyrrolidone or NVP), N-vinyl-N-methyl acetamide, N-vinyl-N-ethyl acetamide, N-vinyl-N-ethyl formamide, N-vinyl formamide. In one embodiment, the hydrophilic vinyl-containing monomers comprise NVP, N-vinyl-N-methyl acetamide or mixtures thereof.

"Acrylic-type" or "acrylic-containing" monomers are those monomers containing the acrylic group: (CH$_2$=CRCOX) wherein R is H or CH$_3$, and X is O or N, which are also known to polymerize readily, such as N,N-dimethyl acrylamide (DMA), 2-hydroxyethyl methacrylate (HEMA), glycerol methacrylate, 2-hydroxyethyl methacrylamide, polyethyleneglycol monomethacrylate, methacrylic acid and acrylic acid.

Other hydrophilic monomers that can be employed in the invention include polyoxyethylene polyols having one or more of the terminal hydroxyl groups replaced with a functional group containing a polymerizable double bond. Examples include polyethylene glycol, ethoxylated alkyl glucoside, and ethoxylated bisphenol A reacted with one or more molar equivalents of an end-capping group such as isocyanatoethyl methacrylate ("IEM"), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

In one embodiment the hydrophilic monomer comprises at least one of DMA, HEMA, glycerol methacrylate, 2-hydroxyethyl methacrylamide, NVP, N-vinyl-N-methyl acrylamide, N-methyl-N-vinylacetamide, polyethyleneglycol monomethacrylate, methacrylic acid and acrylic acid. In one embodiment the hydrophilic monomer comprises DMA.

Examples of hydrophilic components which are useful for the present invention include, but are not limited to HEMA, NVP, DMA, acrylic acid, N-vinyl-N-methyl acetamide, glycerol methacrylate; 2-hydroxyethyl methacrylamide, N-vinyl-N-methyl acrylamide, polyethyleneglycol monomethacrylate, methacrylic acid, polymers and copolymers comprising any of the foregoing and combinations thereof. In one embodiment, the resulting lens is non-ionic. In this embodiments examples of suitable hydrophilic components include HEMA, NVP, DMA, N-vinyl-N-methyl acetamide, glycerol methacrylate, 2-hydroxyethyl methacrylamide, N-vinyl-N-methyl acrylamide, polyethyleneglycol monomethacrylate, polymers and compolymers comprising any of the foregoing and combinations thereof.

Non-limiting examples of suitable soft contact lens formulations of include polymers and copolymers of poly(meth)acrylates, including but not limited to silicone (meth)acrylates; poly(meth)acrylamides, polyvinylcarbonates, polyvinylcarbamates, polyvinylamides, polyvinyllactams, polyurethanes, polyvinyl alcohols and combinations thereof, and the like.

The reaction mixtures also comprise at least one hydrophobic component. Hydrophobic components are those which when mixed, at 25° C. in a 1-1 ratio by volume with neutral, buffered water (pH about 7.0) form an immiscible mixture.

Examples of suitable hydrophobic components include silicone containing components, fluorine containing components, components comprising aliphatic hydrocarbon groups having at least 3 carbons, combinations thereof and the like.

The term component includes monomers, macromers and prepolymers. "Monomer" refers to lower molecular weight compounds that can be polymerized to higher molecular weight compounds, polymers, macromers, or prepolymers. The term "macromer" as used herein refers to a high molecular weight polymerizable compound. Prepolymers are partially polymerized monomers or monomers which are capable of further polymerization.

Suitable fluorine components include at least two, and in some embodiments at least 3 fluorine groups and in some embodiments from 3 to 100 fluorine atoms.

A "silicone-containing component" is one that contains at least one [—Si—O—] unit in a monomer, macromer or prepolymer. Preferably, the total Si and attached 0 are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups. Examples of silicone-containing components which are useful in this invention may be found in U.S. Pat. Nos. 3,808,178; 4,120,570; 4,136,250; 4,153,641; 4,740,533; 5,034,461 and 5,070,215, and EP080539. These references disclose many examples of olefinic silicone-containing components.

Suitable silicone containing components include compounds of Formula I

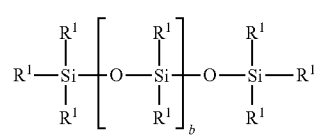

where

R¹ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one R¹ comprises a monovalent reactive group, and in some embodiments between one and 3 R¹ comprise monovalent reactive groups.

As used herein "monovalent reactive groups" are groups that can undergo free radical and/or cationic polymerization. Non-limiting examples of free radical reactive groups include (methacrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryoxy, (meth)acyamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one R¹ is a monovalent reactive group, and at least 3 R¹ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiMMA"), 2-hydroxy-3-methacryloxypropytoxypropyl-tris(trimethylsiloxy)silane, 3-methacryloxypropyltris(trimethylsiloxy)silane ("TRIS"), 3-methacryloxypropylbis(trimethylsiloxy)methylsilane, 3-methacryloxypropylpentamethyl disiloxane and combinations thereof.

In another embodiment, b is 2 to 20, 3 to 15 or in some embodiments 3 to 10; at least one terminal R¹ comprises a monovalent reactive group and the remaining R¹ are selected from monovalent alkyl groups having 1 to 16 carbon atoms, and in another embodiment from monovalent alkyl groups having 1 to 6 carbon atoms. In yet another embodiment, b is 3 to 15, one terminal R¹ comprises a monovalent reactive group, the other terminal R¹ comprises a monovalent alkyl group having 1 to 6 carbon atoms and the remaining R¹ comprise monovalent alkyl group having 1 to 3 carbon atoms. Non-limiting examples of silicone components of this embodiment include polydialkylsiloxanes, such as (mono-(2-hydroxy-3-methacryloxypropyl)-propyl ether terminated polydimethylsiloxane (400-1000 MW)) ("OH-mP DMS"), monomethacryloxypropyl terminated mono-n-butyl terminated polydimethylsiloxanes (800-1000 MW), ("mPDMS").

In another embodiment b is 5 to 400 or from 10 to 300, both terminal R¹ comprise monovalent reactive groups and the remaining R¹ are independently selected from monovalent alkyl groups having 1 to 18 carbon atoms which may have ether linkages between carbon atoms and may further comprise halogen.

In another embodiment, one to four R¹ comprises a vinyl carbonate or carbamate of the formula:

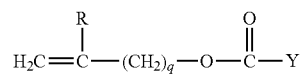

Formula II wherein: Y denotes O—, S— or NH—,
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris (trimethylsiloxy)silane]; 3-[tris(trimethylsiloxy)silyl]propyl allyl carbamate; 3-[tris(trimethylsiloxy)silyl]propyl vinyl carbamate; trimethylsilylethyl vinyl carbonate; trimethylsilylmethyl vinyl carbonate, and

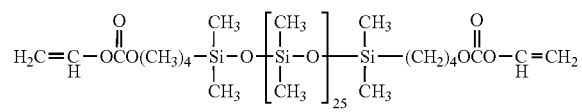

Where biomedical devices with modulus below about 200 are desired, only one R¹ shall comprise a monovalent reactive group and no more than two of the remaining R¹ groups will comprise monovalent siloxane groups.

In one embodiment, where a silicone hydrogel lens is desired, the lens of the present invention will be made from a reactive mixture comprising at least about 20 and preferably between about 20 and 70% wt silicone containing components based on total weight of reactive monomer components from which the polymer is made.

Another class of silicone-containing components includes polyurethane macromers of the following formulae:

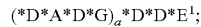

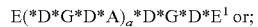

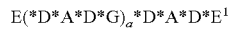  Formulae IV-VI wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

$_a$ is at least 1,

A denotes a divalent polymeric radical of formula:

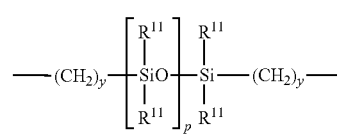

Formula VII $R^{11}$ independently denotes an alkyl or fluoro-substituted alkyl group having 1 to 10 carbon atoms which may contain ether linkages between carbon atoms; y is at least 1, and p provides a moiety weight of 400 to 10,000; each of E and $E^1$ independently denotes a polymerizable unsaturated organic radical represented by formula:

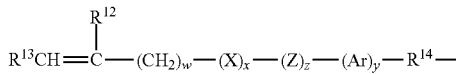

Formula VIII wherein $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

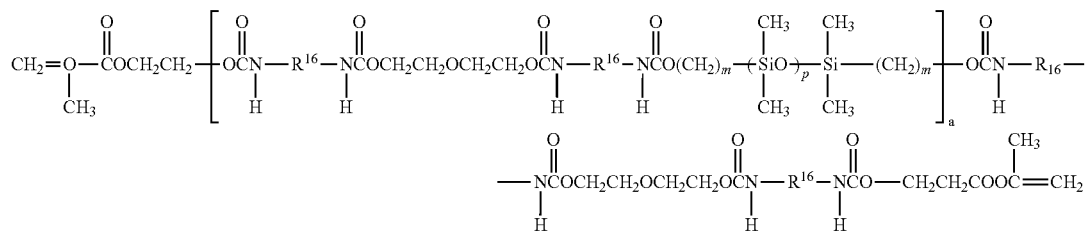

Formula IX wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Any of the foregoing polysiloxanes can also be used as the silicone containing component in this invention.

Other components such as reactive and non-reactive wetting agents disclosed in US-2003-0162862, US05/06640, US2006-0072069, WO2006/039276 may also be included. When wetting agents are used it may also be desirable to include a compatibilizing component. Suitable compatibilizing components include those meeting the compatibility test disclosed in US-2003-0162862. Any of the silicone components described above may be converted into compatibilizing components by incorporating compatibilizing groups, such as hydroxyl groups, in their structure. In some embodiments, the Si to OH ratio is less than about 15:1, and in others between about 1:1 to about 10:1 Non-limiting examples of compatibilizing components include (mono-(2-hydroxy-3-methacryloxypropyl)-propyl ether terminated polydimethylsiloxane (400-1000 MW)), "OH-mPDMS", 2-methyl-,2-hydroxy-3-[3-[1,3,3,3-tetramethyl-1-[(trimethylsilyl)oxy] disiloxanyl]propoxy]propyl ester "SiMMA", 2-hydroxy-3- methacryloxypropyloxypropyl-tris(trimethylsiloxy)silane, bis-3-methacryloxy-2-hydroxypropyloxypropyl polydimethylsiloxane combinations thereof and the like.

Alternatively, the reactive mixture may comprise a prepolymer as disclosed in U.S. Pat. No. 6,846,892 or WO2003/003073.

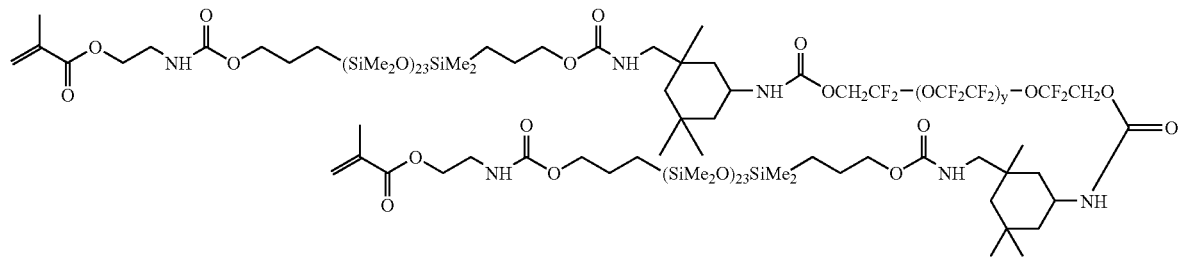

Formula X

Other silicone containing components suitable for use in this invention include those described is WO 96/31792 such as macromers containing polysiloxane, polyalkylene ether, diisocyanate, polyfluorinated hydrocarbon, polyfluorinated ether and polysaccharide groups. U.S. Pat. Nos. 5,321,108; 5,387,662 and 5,539,016 describe polysiloxanes with a polar fluorinated graft or side group having a hydrogen atom attached to a terminal difluoro-substituted carbon atom. US 2002/0016383 describe hydrophilic siloxanyl methacrylates containing ether and siloxanyl linkanges and crosslinkable monomers containing polyether and polysiloxanyl groups.

A polymerization catalyst may be included in the reaction mixture. The polymerization initiators includes compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like, Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitiators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998. The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DMBAPO), and in another embodiment the method of polymerization initiation is via visible light activation. A preferred initiator is bis(2,4,6-trimethylbenzoyl)-phenyl phosphine oxide (Irgacure 819®).

The reactive components may be mixed neat to form a xerogel, or may be mixed with at least one diluent. Suitable diluents for conventional and silicone hydrogel contact lenses are well known and any diluent known to be suitable may be used.

The reactive mixture of the present invention may be cured via any known process for molding the reaction mixture in the production of contact lenses, including spincasting and static casting. Spincasting methods are disclosed in U.S. Pat. Nos. 3,408,429 and 3,660,5457 and static casting methods are disclosed in U.S. Pat. Nos. 4,113,224 and 4,197,266. In one embodiment, the contact lenses of this invention are formed by the direct molding of the silicone hydrogels, which is economical, and enables precise control over the final shape of the hydrated lens. For this method, the reaction mixture is placed in a mold having the shape of the final desired silicone hydrogel, i.e. water-swollen polymer, and the reaction mixture is subjected to conditions whereby the monomers polymerize, to thereby produce a polymer in the approximate shape of the final desired product.

The lenses of the present invention may be coated or uncoated. If the lenses are coated, they may be coated: with a number of agents that are used to coat lens. For example, the coating procedures, compositions, and methods of WO031/11551,U.S. Pat. Nos. 6,087,415, 5,779,943, 5,275,838, 4,973,493, 5,135,297, 6,193,369, 6,213,604, 6,200,626, and 5,760,100 may be used and these applications and patents are hereby incorporated by reference for those procedures, compositions, and methods.

The lenses of the present invention also possess several other desirable properties, such as a percent haze that is less than about 200%, in some embodiments less than about 150% and in others less than about 100%. Percent haze is measured using the following method. The haze is measured by placing a hydrated test lens in borate buffered saline in a clear 20×40×10 mm glass cell at ambient temperature above a flat black background illuminating from below so with a fiber optic lamp (Titan Tool Supply Co. fiber optic light with 0.5" diameter light guide set at a power setting of 4-5, 4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 1.0 software. The -subtracted scattered light image is quantitatively analyzed, by integrating over the central 10 mm of the lens, and then comparing to a CSI Thin Lens®, (CSI Flexible Wear (crotofilcon A) lot ML 62900207 Power—1.0) which is arbitrarily set at a haze value of 100. Four lenses are analyzed and the results are averaged to generate a haze value as a percentage of the standard CSI lens.

In some embodiments the lenses may also possess other desirable characteristics, such as a modulus of less than about 200 psi, in some embodiments less than about 150 psi, and in still others less than about 100 psi. When the lens formulation comprises at least one silicone-containing component, the resulting lens may desirably have oxygen transmissibility of greater than about 50 barrers and in other embodiments greater than about 100 barrers.

Many of the lens formulations cited above may allow a user to insert the lenses for a continuous period of time ranging from one day to thirty days. It is known that the longer a lens is on the eye, the greater the chance that bacteria and other microbes will build up on the surface of those lenses. Therefore there is a need to develop lenses that release antimicrobial agents such as silver, over an extended period of time.

The invention includes an antimicrobial lens comprising, consisting of, or consisting essentially of, a metal salt wherein the molar solubility of the metal ion in pure water at about 25° C. is greater than about $2.0\times10^{-30}$ moles/L to about less than about 20 moles/L. The preferred metal salts are silver salts where the silver ion has a molar solubility of greater than about $2.0\times10^{-17}$ moles/L to less than about 0.04 moles/L. When an ionizable antimicrobial metal compound is used, in some embodiments the metal cation of the ionizable antimicrobial metal compound will have a molar solubility of greater than about $2.0\times10^{-17}$ moles/L to less than about 0.04 moles/L.

The terms antimicrobial lens and metal salt have their aforementioned meanings and preferred ranges. As used herein, the term "pure" refers to the quality of the water used as defined in the CRC Handbook of Chemistry and Physics, $74^{th}$ Edition, CRC Press, Boca Raton Fla., 1993. The term "molar solubility" refers to the number of moles of metal dissolved or dissociated from the anion per liter of water. This number is derived from the solubility-product constant ($K_{sp}$) measured in pure water at 25° C. (See Skoog, D. A. et al. FUNDAMENTALS OF ANALYTICAL CHEMISTRY, Fifth Edition, Saunders College Publishing, New York, 1988, see also, published values in CRC Handbook of Chemistry and Physics, $74^{th}$ Edition, CRC Press, Boca Raton Fla., 1993) For example, if the metal salt is silver carbonate ($Ag_2CO_3$), the $K_{sp}$ is expressed by the following equation $$Ag_2CO_3(s) \rightarrow 2Ag^+(aq) + CO_3^{2-}(aq)$$

The $K_{sp}$ is calculated as follows

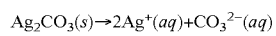

As silver carbonate dissolves, there is one carbonate anion in solution for every two silver cations, $[CO_3^{2-}] = \frac{1}{2}[Ag^+]$, and the solubility-product constant equation can be rearranged to solve for the dissolved silver concentration as follows $$K_{sp}=[Ag^+]^2(\tfrac{1}{2}[Ag^+])=\tfrac{1}{2}[Ag^+]^3$$

$$[Ag^+]=(2K_{sp})^{1/3}$$

The $K_{sp}$ may be used to calculate the molar solubility of any metal salt as follows $$\text{For } MX\colon [M]=(K_{sp})^{1/2}$$

$$\text{For } M_2X\colon [M]=(2K_{sp})^{1/3}$$

$$\text{For } M_3X\colon [M]=(3K_{sp})^{1/4}$$

Metal salts having a metal ion with a molar solubility of about greater than about $2\times10^{-30}$ moles/L to less than about 20 moles/L when measured at 25° C. will continuously release the metal from lenses for a period of time from one day to up to or longer than a thirty day period. The preferred metal salts of the invention are silver salts, wherein the molar solubility of the silver ion is greater than or equal to about $2\times10^{-17}$ moles/L. The preferred molar solubility is greater than or equal to about $9\times10^{-9}$ moles/L to less than or equal to $1\times10^{-5}$ moles/L when measured at 25° C. The preferred metal salts of this invention are silver iodide, silver chloride and silver bromide, where silver iodide is particularly preferred.

Still yet further, the invention includes a method of reducing the adverse events associated with microbial colonization on a lens placed in the ocular regions of a mammal comprising, consisting of, or consisting essentially of, placing an antimicrobial lens comprising a metal salt on the eye of a mammal. The terms lens, antimicrobial lens, and metal salt all have their aforementioned meanings and preferred ranges. The phrase "adverse events associated with microbial colonization" include but are not limited to contact ocular inflammation, contact lens related peripheral ulcers, contact lens associated red eye, infiltrative keratitis, microbial keratitis, and the like. The term mammal means any warm blooded higher vertebrate, and the preferred mammal is a human.

Still yet even further, the invention includes a method of producing an antimicrobial lens comprising, consisting essentially of, or consisting of a metal salt wherein the method comprises, consists essentially of or consists of mixing the metal salt with a lens formulation and curing the lens formulation/metal salt mixture to form a lens. The term "formulation" includes any ingredient or combination of ingredients that is used to make antimicrobial lenses, such as monomer, pre-polymers, co-polymers, macromers, initiators, pigments, dyes, UV absorbing agents and the like. Examples of such ingredients are known in the art and some of those ingredients are disclosed in the ophthalmic lens patents and patent applications cited earlier in this application.

The antimicrobial metal salts may be incorporated into the tenses of the present invention by numerous methods including the method comprising, consisting essentially of, or consisting of the steps of (a) mixing a salt precursor with a lens formulation having a hydrophilicity index of at least about 42;
(b) forming the lens; and
(c) treating the lens with a metal agent.

The term "salt precursor" refers to any compound or composition (including aqueous solutions) that contains a cation that may be substituted with metal ions. It is preferred that the salt precursor is soluble an lens formulation at about 1 µg/mL or greater. The term salt precursor does not include zeolites as described in WO03/11351, solid silver as described in WO02/62402. The preferred amounts of salt precursor in the lens is about 0.00001 to about 10.0 weight percent, more preferably about 0.0001 to about 1.0 weight percent, most preferably about 0.001 to about 0.1 weight percent based upon the total weight of the monomer composition. Examples of salt precursors include but are not limited to inorganic molecules such as sodium chloride, sodium iodide, sodium bromide, lithium chloride, lithium sulfide, sodium sulfide, potassium sulfide, sodium tetrachloro argentate, and the like. Examples of organic molecules include but are not limited to tetra-alkyl ammonium lactate, tetra-alkyl ammonium sulfate, quaternary ammonium halides, such as tetra-alkyl ammonium chloride, bromide or iodide. The preferred precursor salt is sodium iodide.

The term "forming" refers to any of a number of methods used to form lenses that include but are not limited to curing with light or heat. The lens formulations of the present invention can be formed by any of the methods know to those skilled in the art, such as shaking or stirring, and used to form polymeric articles or devices by known methods.

For example, the ophthalmic devices of the invention may be prepared by mixing reactive components and any diluent(s) with a polymerization initiator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the lens formulation in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The preferred method for producing contact lenses of this invention is by molding. For this method, the lens formulation is placed in a mold having the shape of the final desired lens, and the lens formulation is subjected to conditions whereby the components polymerize, to produce a lens. The lens may be treated with a solvent to remove the diluent and ultimately replace it with water. This method is further described in U.S. Pat. Nos. 4,495,313; 4,680,336; 4,889,664; and 5,039,459 incorporated herein by reference. The preferred method of curing is with radiation, preferably UV or visible light, and most preferably with visible light.

The term "metal agent" refers to any composition (including aqueous solutions) containing metal ions. Examples of such compositions include but are not limited to aqueous or organic solutions of silver nitrate, silver triflate, or silver acetate, where the concentration of metal agent in solution is about 1 µg/mL or greater. The preferred metal agent is aqueous silver nitrate, where the concentration of silver nitrate is the solution is about greater than or equal to 0.0001 to about 2 weight percent more preferably about greater than 0.001 to about 0.01 weight percent based on the total weight of the solution. The term "treating" refers to any method of contacting the metal agent with the lens, where the preferred method is immersing the lens in a solution of the metal agent. Treating can include heating the lens in a solution of the metal agent, but it preferred that treating is carried out at ambient temperatures.

Yet even further, the invention includes a method of preparing an antimicrobial lens comprising, consisting essentially of, or consisting of a metal salt, wherein the method comprises, consists essentially of, or consists of the steps of (a) mixing a metal precursor with a lens formulation comprising a hydrophilicity index of at least about 42;
(b) forming the lens; and
(c) treating the lens with an anion precursor.

The term metal precursor refers to any composition (including aqueous solutions) that contains a metal cation and a counter anion wherein the counter anion may be substituted. Examples of metal precursors include but are not limited to silver triflate, copper nitrate, copper sulfate, magnesium sulfate, zinc sulfate, and the like. The preferred metal precursor is silver triflate. The term anion precursor refers to any composition (including aqueous solutions) that contains an anion that may be substituted with the anion of the metal precursor to form a metal salt. Examples of anion precursors include but are not limited to inorganic molecules such as sodium chloride, sodium iodide, sodium bromide, lithium chloride, lithium sulfide, sodium sulfide, potassium sulfide and the like. Examples of anion precursors that are organic molecules include but are not limited to tetra-alkyl ammonium lactate, tetra-alkyl ammonium sulfate, quaternary ammonium halides, such as tetra-alkyl ammonium chloride, bromide or iodide. The preferred anion precursor is aqueous sodium iodide.

And yet even further, the invention includes a method of preparing an antimicrobial lens comprising, consisting essentially of, or consisting of a metal salt, wherein the method comprises, consists essentially of, or consists of the steps of
(a) treating a cured lens formed from a lens formulation having a hydrophilicity index of at least about 42 with a salt precursor;
(b) treating the lens of step (a) with a metal agent.

Still, yet even further, the invention includes a method of preparing an antimicrobial lens comprising, consisting essentially of, or consisting of a metal salt, wherein the method comprises, consists essentially of, or consists of the steps of
(a) mixing a metal with a lens formulation having a hydrophilicity index of at least about 42;
(b) forming the lens;
(c) treating the lens of step (b) with an oxidizing agent; and
(d) treating the lens of step (c) with an anion precursor.

The term "metal" refers to any metal having an oxidation state of zero. Examples of metals include but are not limited to aluminum, cobalt, calcium, magnesium, nickel, titanium, vanadium, strontium, iron, gold, silver, palladium, platinum, copper, manganese and zinc. The preferred metals are manganese, zinc, copper, gold, platinum, palladium and silver, the particularly preferred metal is silver. The term "oxidizing agent" includes but in not limited know agents such as hydrogen peroxide and the like.

All of the aforementioned processes may be carried out by a single mechanical device or a combination of mechanical devices. For example, if metal salts are added to cured lenses, all of the steps to add those metal alts may be carried out on a hydration machine which functions as follows. A cured lens (non-hydrated, partially hydrated or fully hydrated lens) may be placed in a single blister package. A solution of a salt precursor is added to this package and left for a time sufficient to allow the desired amount of salt precursor to be incorporated into the lens, but insufficient to produce discoloration or haze. The time will vary depending upon the solubility and concentration of the salt and temperature. Suitable times (at ambient temperature) include up to about 30 minutes and preferably between about 30 seconds and 5 minutes and more preferably about two minutes. Subsequently, the solution of the salt precursor is removed and a solution of a metal agent is added to the package. The soak time for the metal agent can be selected using the solubility, concentration and temperature. Subsequently the metal agent solution is removed and the lens is washed with several portions deionized water, followed by sterilization.

Still yet even further, the invention includes a method of preparing an antimicrobial lens comprising, consisting essentially of, or consisting of a metal salt, wherein the method comprises, consists essentially of, or consists of the steps of
(a) treating a cured lens formed from a lens formulation having a hydrophilicity index of at least about 42 with a metal agent.
(b) treating the lens of step (a) with a salt precursor;

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

The following test methods were used in the present examples.

The water content was measured as follows: lenses to be tested are allowed to sit in packing solution for 24 hours. Each of three test lens are so removed from packing solution using a sponge tipped swab and placed on blotting wipes which have been dampened with packing solution. Both sides of the lens are contacted with the wipe. Using tweezers, the test lens are placed in a weighing pan and weighed. The two more sets of samples are prepared and weighed as above pan is weighed three times and the average is the wet weight.

The dry weight is measured by placing the sample pans in a vacuum oven which has been preheated to 60° C. for 30 minutes. Vacuum is applied until at least 0.4 inches Hg is attained. The vacuum valve and pump are turned off and the lenses are dried for four hours. The purge valve is opened and the oven is allowed reach atmospheric pressure. The pans are removed and weighed. The water content is calculated as follows:

Wet weight=combined wet weight of pan and lenses−weight of weighing pan

Dry weight = combined dry weight of pan and lens − weight of weighing pan $$\% \text{ water content} = \frac{(\text{wet weight} - \text{dry weight})}{\text{wet weight}} \times 100$$

The average and standard deviation of the water content are calculated for the samples are reported.

Wettability is measured by measuring the dynamic contact angle or DCA, typically at 23° C., with borate buffered saline, using a Wilhelmy balance. The wetting force between the lens surface and borate buffered saline is measured using a Wilhelmy microbalance while the sample strip cut from the center portion of the lens is being immersed into or pulled out of the saline at a rate of 100 microns/sec. The following equation is used $$F=2\gamma p \cos \theta \text{ or } \theta=\cos^{-1}(F/2\gamma p)$$

where F is the wetting force, γ is the surface tension of the probe liquid, p is the perimeter of the sample at the meniscus and θ is the contact angle. Typically, two contact angles are obtained from a dynamic wetting experiment—advancing contact angle and receding contact angle. Advancing contact angle is obtained from the portion of the wetting experiment where the sample is being immersed into the probe liquid, and these are the values reported herein. At least four lenses of each composition are measured and the average is reported.

Oxygen permeability (Dk) was determined by the polarographic method generally described in ISO 9913-1; 1996(E), but with the following variations. The measurement is conducted at an environment containing 2.1% oxygen. This environment is created by equipping the test chamber with nitrogen and air inputs set at the appropriate ratio, for example 1800 ml/min of nitrogen and 200 ml/min of air. The t/Dk is calculated using the adjusted $p_{O2}$. Borate buffered saline was used. The dark current was measured by using a pure humidified nitrogen environment instead of applying MMA lenses. The lenses were not blotted before measuring. Four lenses were stacked instead of using lenses of varied thickness. A curved sensor was used in place of a flat sensor. The resulting Dk value is reported in barrers.

Modulus is measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck"[5] width is loaded into the grips and elongated at a constant rate of strain of 2 in/min. until it breaks. The initial gauge length of the sample (Lo) and sample length at break (Lf) are measured. Twelve specimens of each composition are measured and the average is reported. Tensile modulus is measured at the initial linear portion of the stress/strain curve.

The % Si was calculated based upon the structure and molecular weight of the compound.

It will be appreciated that all of the tests specified herein have a certain amount of inherent test error. Accordingly, results reported herein are not to be taken as absolute numbers, but numerical ranges based upon the precision of the particular test.

EXAMPLES

The following abbreviations were used in the examples ac
PDMS=bis-3-acryloxy-2-hydroxypropyloxypropyl polydimethylsiloxane (MW 20007 acrylated polydimethylsiloxane) from Degussa
Blue HEMA=the reaction product of reactive blue number 4 and HEMA, as described in Example 4 or U.S. Pat. No. 5,944,853
CGI 1850=1:1 (w/w) blend of 1-hydroxycyclohexyl phenyl ketone and bis(2,6-dimethyoxybenzoyl)-2,4-4-trimethylpentyl phosphine oxide
CGI 819=bis(2,4,6-trimethylbenzoyl)-phenylphosphineoxide
DI water=deionized water
D3O=3,7-dimethyl-3-octanol
DMA=N,N-dimethylacrylamide
EGDMA=ethyleneglycol dimethacrylate
HEMA=hydroxyethyl methacrylate
IPA=Isopropyl alcohol
MAA=methacrylic acid
Macromer=Macromer prepared according to the procedure disclosed under Macromer Preparation in Example 1, of US-2003-0052424-A1
MC=methyl cellulose
mPDMS=mono-methacryloxypropyl terminated polydimethylsiloxane (MW 800-1000)
Norbloc=2-(2'-hydroxy-5-methacrylyloxyethylphenyl)-2H-benzotriazole
ppm=parts per million micrograms of sample per gram of dry lens
OH mPPDMS=mono-(3-methacryloxy-2-hydroxypropyloxy)propyl terminated, monobutyl terminated polydimethylsiloxane
PVP=polyvinylpyrrolidinone (K 90)
PVP 2500=polyvinylpyrrolidinone (MW 2500)
SiMMA=3-methacryloxy-2-hydroxypropyloxy)propylbis (trimethylsiloxy)methylsilane
SSPS=Sodium Sulfate Packaging Solution
TAA=t-amyl alcohol
TEGDMA=tetraethyleneglycol dimethacrylate
w/w=weight/total weight
w/v=weight/total volume
v/v=volume/total volume
3M3P=3-methyl-3-pentanol.

The following compositions were prepared for use

| Sodium Sulfate Packaging Solution (SSPS) | |
|---|---|
| Components | Specifications |
| Water (mL) | 1,000 |
| Sodium Sulfate (g) | 14 ± 0.02 |
| Sodium Borate (g) | 1.85 ± 0.02 |
| Boric Acid (g) | 9.26 ± 0.02 |
| Methylcellulose 4000 Centipoises (g) | 0-0.10 |

Examples 1-9

Hydrogel blends were made from the monomer mixtures shown in Table 1, below, and using the conditions described below. All amounts were calculated as weight percent based upon the weight of all component in the monomer mixture, excluding diluent. The reactive components were mixed with the diluents listed for at least two hours prior to use and degassed for 15 minutes at 127 rpm and 25° C. under 20 mmHg (27 mbar). The amount of diluent used, based upon the weight % of all reactive components and diluent is listed as % diluent.

TABLE 1

| Monomers | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| MPDMS | 31.0 | 31.0 | 31.0 | 25.0 | 25.0 | 22.0 | 27.0 | 31.0 | — |
| OH mPDMS | — | — | — | — | — | — | — | — | 45.54 |
| SiMAA2 | 28.0 | 28.0 | 28.0 | 30.0 | 30.0 | 30.0 | 30.0 | 27.0 | — |
| AcPDMS | — | — | — | 5.0 | 5.0 | — | 5.0 | — | — |
| TEGDMA | 1.5 | — | 1.5 | 0.5 | 0.5 | — | — | 1.5 | — |
| EGDMA | — | — | — | — | — | 0.75 | — | — | — |
| Macromer | — | — | — | — | — | — | — | — | 6.93 |
| DMA | 24.0 | 25.5 | 24.0 | 20.0 | 20.0 | 20.0 | 20.0 | 25.0 | 19.8 |
| HEMA | 6.0 | 6.0 | 5.25 | 8.65 | 10.25 | 19.5 | 7.15 | 6.0 | 12.41 |
| PVP K-90 | 7.0 | 7.0 | 7.0 | 7.0 | 7.0 | 6.0 | 7.0 | 7.0 | 11.88 |
| MAA | — | — | 1.0 | 1.6 | — | — | 1.6 | — | 0.99 |
| CGI 1850 | 0.48 | 0.48 | — | — | — | — | — | 0.48 | — |
| CGI 819 | — | — | 0.23 | 0.23 | 0.23 | 0.23 | 0.23 | — | 0.25 |

TABLE 1-continued

| Monomers | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Norbloc | 2.0 | 2.0 | 2.0 | 2.0 | 2.0 | 1.5 | 2.0 | 2.0 | 2.18 |
| Blue HEMA | 0.02 | 0.02 | 0.02 | 0.02 | 0.02 | 0.02 | 0.02 | 0.02 | 0.02 |
| % Diluent | 23 | 23 | 23 | 40 | 40 | 40 | 40 | 40 | 44.75 |
| D3O | 100 | 100 | 100 | — | — | — | — | 100 | — |
| TAA | — | — | — | 72.5 | 72.5 | 72.5 | 72.5 | — | 80 |
| PVP 2500 | — | — | — | 27.5 | 27.5 | 27.5 | 27.5 | — | 20 |

The monomer mixes listed in Table 1, above were charged into the lens molds listed in Table 2 and cured under visible light (Philips TL-03 bulbs) in a nitrogen atmosphere (<0.5% $O_2$) @45±5° C. The mold materials, cure times and cure profiles are listed in Table 2, below. The lenses were released from the molds and solvent exchanged using the release/solvent exchange procedures noted in Table 2. After release the lenses were placed in jar of sodium iodide solution (>3 mL per lens) having a nominal NaI concentration in DI/MC as listed in Table 2, and rolled on a jar roller for at least 8 hours. The lenses were individually transferred onto blister bowls, and the accompanying sodium iodide solution was removed. A solution of silver nitrate was added to the bowls (800 μL per lens of 150 μg/mL silver nitrate in deionized water). After two minutes of exposures the silver nitrate solution was removed, and the lenses transferred into a jar of DI/MC for a 30-minute rinse on a jar roller. The rinse step was repeated five more times (30 minutes per rinse) using fresh DI/MC solution. The lenses were equilibrated in a jar of SSPS, and packaged in 950+/−50 uL of SSPS using polypropylene bowls and foil, and autoclaved once (122.5° C., 30 minutes).

TABLE 2

| Ex # | FC/BC material | Cure temp (° C.) | Cure profile (min @ mW/cm²) | Release cond. | Nominal NaI (μg/mL) |
|---|---|---|---|---|---|
| 1 | Zeonor Finacene | 45 | 8 @ 0.8<br>4 @ 4 | 1 | 40 |
| 2 | Zeonor Zeonor | 45 | 0.5 @ 0.5<br>1.5 @ 1<br>1.5 @ 3<br>1.5 @ 4<br>1.5 @ 6.2 | 1 | 300 |
| 3 | Zeonor Finacene | 45 | 0.5 @ 0.5<br>1.5 @ 1<br>1.5 @ 3<br>1.5 @ 4<br>1.5 @ 6.2 | 2 | 300 |
| 4 | Zeonor Zeonor | 80 | 0.167 @ 1-2<br>6.833 @ 4 | 2 | 150 |
| 5 | Zeonor Zeonor | 80 | 0.167 @ 1-2<br>6.833 @ 4 | 3 | 300 |
| 6 | Zeonor Zeonor | 80 | 0.167 @ 1-2<br>6.833 @ 4 | 3 | 300 |
| 7 | Zeonor Zeonor | 80 | 0.167 @ 1-2<br>6.833 @ 4 | 3 | 500 |
| 8 | Zeonor Blend* | 80 | 0.5 @ 1<br>5.33 @ 1.8<br>5.33 @ 6 | 4 | 450 |
| 9 | Zeonor Blend* | 80 | 2.67 @ 1.5<br>5.33 @ 6 | 4 | 900 |

*Blend was a 55 wt % Zeonor/45 wt % polypropylene blend

Release and solvent exchange procedures:
Procedure 1: The molds were opened, and the lenses released in 70% IPA in DI water. After 60 minutes the lenses were transferred into: i) 100% IPA for 60 minutes; ii) 70% IPA in DE water for 60 minutes; iii) 10% IPA in DI water for 30 minutes; iv) DI water for 30 minutes; v) DI water with 50 ppm methyl cellulose (DI/MC) for 30 minutes, then stored in fresh DI/MC.

Procedure 2. The molds were opened, and the lenses released in 70% IPA in DI water over 60 minutes. After two additional changeouts of 70% IPA in DI water (60 minutes each) the lenses were transferred into: i) DI water for 30 minutes; DI water with 50 ppm methyl cellulose (DI/MC) for 30 minutes, then stored in fresh DI/MC.

Procedure 3. The molds were opened, and the lenses equilibrated in DI water over 30 minutes, The lenses were releases in 70% IPA in DI water (≧30 minutes), rinsed in DI water (≧5 minutes), and equilibrated in DI water (30 minutes, 45±5 C).

Procedure 4 The molds were opened, and the lenses released in 70% IPA in DI water. After 60 minutes the lenses were transferred into: i) 100% IPA for 60 minutes; ii) 70% IPA in DI water for 60 minutes; iii) DI water for 30 minutes; iv) DI water for 30 minutes, v) staged in fresh DI water (30 minutes, 45±5° C.).

The water content, advancing contact angle, % Silicon, silver content, Dk and modulus were measured and are shown in Table 3, below.

TABLE 3

| Ex. # | % $H_2O$ | Adv. contact angle | % Si | Average Ag/lens (ug) | Dk | Modulus (psi) |
|---|---|---|---|---|---|---|
| 1 | 37 | NT | 15 | 0.2 | 103 | 100 |
| 2 | 47 | 60 | 15 | 4.3 | 108 | 40 |
| 4 | 42 | 60 | 15 | 2.0 | 95 | 78 |
| 5 | 48 | 46 | 15 | 1.5-2.1 | 82 | 92 |
| 6 | 39 | NT | 13 | 2.8-3.4 | 91 | 96 |
| 7 | 39 | NT | 12 | 2.8-3.1 | 46 | 118 |
| 8 | 51 | 71 | 15 | 3.5-4.9 | 92 | 83 |
| 9 | 44 | 82 | 14 | 4.9-5.6 | 93 | 50 |
| 10 | 61 | 70 | 14 | 4.6-5.4 | 55 | 42 |

Example 10

It had been found in prior studies that lenses made according to Example 1 would exhibit unacceptable movement on the Josephson push up test in a small percentage of patients when measured after about 8 hours of wear. Patients who experienced unacceptable lens movement consistently experienced unacceptable movement in subsequent trials while those who demonstrated acceptable movement in the Josephson push up test, up and forward gaze assessments also consistently did so. The following study was conducted to identify patients who experienced poor lens movement for use as screeners in subsequent examples reported below. Lenses made according to Example 1 and clinically evaluated against contact lenses of the same formulation, but without any silver iodide. The clinical evaluation was a double masked, randomized, bilateral cross-over study with 14 patients completing the study. The lenses were worn for at least 8 hours. The purpose of the study was to identify patients who experienced poor movement with the lenses of Example 1. After about eight hours lens movement was evaluated using the Josephson push up test, described in detail in Contact Lens Practice, Chapman & Hall, 1994, edited by M. Ruben and M. Guillon, pgs. 589-99 and using the following ratings 2=excessive movement, 1=moderate movement, 0=optimal movement, −1=minimal movement; and a −2 does not move at all, Two patients were identified as experiencing movement of less than −1.

Example 11

The lenses of Examples 2-9 were clinically evaluated on the two patients identified in Example 10 to experience poor movement. Each lens was evaluated in a single masked (subject) study. Each lens set was worn for one day for 8 to 12 hours. At the end of the day lens movement was evaluated for each lens using the Josephson push up test. In this Example, movement results of at least −1 were considered acceptable. The results are shown in Table 4, below.

TABLE 4

| Lens Ex # | Hydrophilicity Index | % acceptable movement |
|---|---|---|
| 2 | 42 | 0* |
| 3 | 46 | 100 |
| 4 | 47 | 100 |
| 5 | 38 | 50 |
| 6 | 40 | 50 |
| 7 | 46 | 100 |
| 8 | 41 | 75 |
| 9 | 54 | 100 |

*Data from one patient only.

As shown in the table above, lenses having a hydrophilicity index of greater than about 42 have consistently acceptable on eye movement (100%), even in patients populations which display a proclivity toward poor lens movement with lenses comprising at least one metal salt. Also, the present invention provides silicone hydrogel contact lenses comprising at least one metal salt which provide acceptable on eye movement in at least about 90% of patients and in some embodiments, at least about 95% of patients.

What is claimed is:

1. A contact lens comprising at least one metal salt and a polymer formed from a reaction mixture comprising at least one hydrophobic component and hydrophilic components in a concentration to provide a hydrophilicity index of at least about 45, wherein said contact lens displays, on at least about 90% of patients, acceptable movement on eye after at least one hour of wear.

2. The lens of claim 1 wherein the formula of the metal salt is $[M]_a [X]_b$ wherein X contains any negatively charged ion, a is $\geq 1$, b is $\geq 1$ and M is any positively charged metal.

3. The lens of claim 2 wherein M is selected from the group consisting of $Al^{+3}$, $Co^{+2}$, $Co^{+3}$, $Ca^{+2}$, $Mg^{+2}$, $Ni^{+2}$, $Ti^{+2}$, $Ti^{+3}$, $Ti^{+4}$, $V^{+2}$, $V^{+3}$, $V^{+5}$, $Sr^{+2}$, $Fe^{+2}$, $Fe^{+3}$, $Au^{+2}$, $Au^{+3}$, $Au^{+1}$, $Ag^{+2}$, $Ag^{+1}$, $Pd^{+2}$, $Pd^{+4}$, $Pt^{+2}$, $Pt^{+4}$, $Cu^{+1}$, $Cu^{+2}$, $Mn^{+2}$, $Mn^{+3}$, $Mn^{+4}$, $Zn^{+2}$ and mixtures thereof.

4. The lens of claim 2 wherein M is selected from the group consisting of $Mg^{+2}$, $Zn^{+2}$, $Cu^{+1}$, $Cu^{+2}$, $Au^{+2}$, $Au^{+3}$, $Au^{+1}$, $Pd^{+2}$, $Pd^{+4}$, $Pt^{+2}$, $Pt^{+4}$, $Ag^{+2}$, $Ag^{+1}$ and mixtures thereof.

5. The lens of claim 2 wherein M is selected from the group consisting of $Zn^{+2}$, $Cu^{+1}$, $Cu^{+2}$, $Ag^{+2}$, $Ag^{+1}$ and mixtures thereof.

6. The lens of claim 2 wherein M comprises $Ag^{+1}$.

7. The lens of claim 2 wherein X is selected from the group consisting of $CO_3^{-2}$, $SO_4^{-2}$, $CH_3CO_2^{-1}$, $PO_4^{-3}$, $Cl^{-1}$, $I^{-1}$, $Br^{-1}$, $S^{-2}$, $O^{-2}$ and mixtures thereof.

8. The lens of claim 2 wherein X is selected from the group consisting of $CO_3^{-2}$, $SO_4^{-2}$, $Cl^{-1}$, $I^{-1}$, $Br^{-1}$ and mixtures thereof.

9. The lens of claim 2 wherein M is silver and X is selected from the group consisting of $CO_3^{-2}$, $SO_4^{-2}$, $Cl^{-1}$, $I^{-1}$, $Br^{-1}$ and mixtures thereof.

10. The lens of claim 1 wherein the metal salt is selected from the group consisting of silver sulfate, silver iodate, silver carbonate, silver phosphate, silver sulfide, silver chloride, silver bromide, silver iodide, silver oxide and mixtures thereof.

11. The lens of claim 1 wherein the metal salt is selected from the group consisting of silver sulfate, silver iodate, silver chloride, silver bromide, and silver iodide and mixtures thereof.

12. The lens of claim 1 wherein the metal salt comprises silver iodide.

13. The lens of claim 1 wherein said reaction mixture comprises hydrophilic components selected from the group consisting of HEMA, NVP, DMA, N-vinyl-N-methyl acetamide, methacrylic acid, glycerol methacrylate, 2-hydroxyethyl methacrylamide, N-vinyl-N-methyl acrylamide, polyethyleneglycol monomethacrylate, polymers and compolymers comprising any of the foregoing and combinations thereof.

14. The lens of claim 1 wherein the diameter of the metal salt particles is less than about ten microns.

15. The lens of claim 3 wherein M is silver and the amount of silver per lens is about 0.00001 to about 10 weight percent.

16. The lens of claim 3 wherein M is silver and the amount of silver per lens is about 0.0001 to about 1.0 weight percent.

17. The lens of claim 3 wherein M is silver and the amount of silver per lens is about 0.001 to about 0.1 weight percent.

18. The lens of claim 16 wherein the metal salt is selected from the group consisting of silver chloride, silver iodide, silver bromide and mixtures thereof.

19. The lens of claim 1 wherein said metal salt comprises a metal ion having a molar solubility in water at about 25 C is greater than or equal to about $2.0 \times 10^{-30}$ moles/L to about less than about 20 moles/L.

20. The lens of claim 19 wherein the molar solubility of the metal ion is greater than or equal to about $1 \times 10^{-17}$ moles/L to less than or equal to 0.04 moles/L when measured at 25° C.

21. The lens of claim 1 wherein said hydrophobic component comprises at least one silicone-containing component.

22. The lens of claim 21 wherein said at least one silicone-containing components is selected from silicones of Formula I

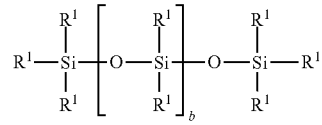

where
R¹ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

23. The lens of claim 21 wherein said at least one silicone containing component is selected from the group consisting of 2-methyl-,2-hydroxy-3-[3-[1,3,3,3-tetramethyl-1-[(trimethylsilyl)oxy]disiloxanyl]propoxy]propyl ester, 2-hydroxy-3-methacryloxypropyloxypropyl-tris(trimethylsiloxy)silane, 3-methacryloxypropyltris(trimethylsiloxy)silane, 3-methacryloxypropyl-bis(trimethylsiloxy)methylsilane, 3-methacryloxypropylpentamethyl disiloxane and combinations thereof.

24. The lens of claim 21 wherein said at least one silicone containing component comprises at least one polydialkylsiloxane.

25. The lens of claim 21 wherein said at least one silicone containing component comprises (mono-(2-hydroxy-3-methacryloxypropyl)-propyl ether terminated polydimethylsiloxane (400-1000 MW), monomethacryloxypropyl terminated mono-n-butyl terminated polydimethylsiloxanes (800-1000 MW), or a combination thereof.

26. The lens of claim 21 wherein said at least one silicone containing component comprises at least one silicone-containing vinyl carbonate, vinyl carbamate, or a mixture thereof.

27. The lens of claim 21, wherein said at least one silicone containing component comprises at least one component selected from the group consisting of polyurethane macromers, macromers containing polysiloxane, polyalkylene ether, diisocyanate, polyfluorinated hydrocarbon, polyfluorinated ether and polysaccharide groups, polysiloxanes with a polar fluorinated graft or side group having a hydrogen atom attached to a terminal difluoro-substituted carbon atom, hydrophilic siloxanyl methacrylates containing ether and siloxanyl linkanges, and crosslinkable monomers containing polyether and polysiloxanyl groups.

* * * * *